United States Patent [19]

Barnacka et al.

(10) Patent No.: US 12,302,056 B2
(45) Date of Patent: *May 13, 2025

(54) VIBROACOUSTIC EARBUD

(71) Applicants: Anna Barnacka, Cambridge, MA (US); Martin D Ring, Ashland, MA (US); John V Cunsolo, Cambridge, MA (US)

(72) Inventors: Anna Barnacka, Cambridge, MA (US); Martin D Ring, Ashland, MA (US); John V Cunsolo, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/653,704

(22) Filed: May 2, 2024

(65) Prior Publication Data

US 2024/0292142 A1    Aug. 29, 2024

Related U.S. Application Data

(63) Continuation of application No. 17/843,926, filed on Jun. 17, 2022, now Pat. No. 12,003,914.

(51) Int. Cl.
*H04R 1/10* (2006.01)
*A61B 8/12* (2006.01)

(52) U.S. Cl.
CPC .......... *H04R 1/1041* (2013.01); *A61B 8/12* (2013.01); *H04R 1/1016* (2013.01); *H04R 1/1075* (2013.01); *H04R 2460/11* (2013.01)

(58) Field of Classification Search
CPC .. H04R 1/1041; H04R 1/1016; H04R 1/1075; H04R 2460/11; A61B 8/12
USPC ........................................................... 381/74
See application file for complete search history.

(56) References Cited

U.S. PATENT DOCUMENTS

| | | | |
|---|---|---|---|
| 11,234,069 B2 * | 1/2022 | Barnacka ................. | A61B 8/12 |
| 11,665,493 B2 * | 5/2023 | Usher ..................... | H04R 25/70 |
| | | | 381/59 |
| 12,003,914 B2 * | 6/2024 | Barnacka ................. | A61B 8/12 |
| 2019/0247010 A1 | 8/2019 | Barnacka | |

* cited by examiner

*Primary Examiner* — Paul Kim
(74) *Attorney, Agent, or Firm* — John Gillis

(57) ABSTRACT

A vibroacoustic earbud ("earbud") is proposed that includes a housing and an infrasonic/vibration sensor. The housing includes a nozzle with a nozzle tip that is configured for positioning within an ear canal of an individual. The sensor is included within the nozzle and detects biosignals including infrasonic signals from a body of the individual in the ear canal. The nozzle tip engages with a wall of the ear canal to provide an earbud seal, the result of which forms an ear canal acoustic volume that amplifies the biosignals. The earbud is tuned/designed to minimize loss of amplitude of the biosignals detected by the sensor in the ear canal acoustic volume when an unintentional leak occurs in the earbud seal that possibly reduces acoustic pressure in the ear canal acoustic volume.

20 Claims, 8 Drawing Sheets

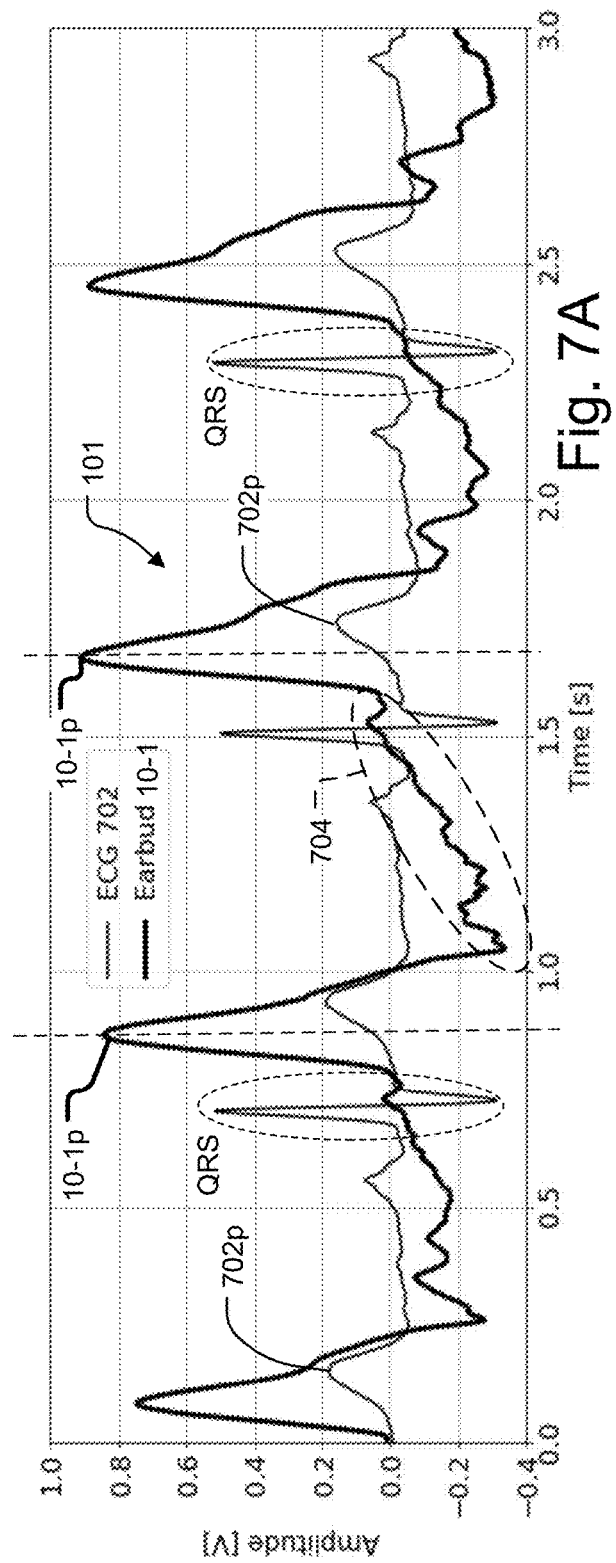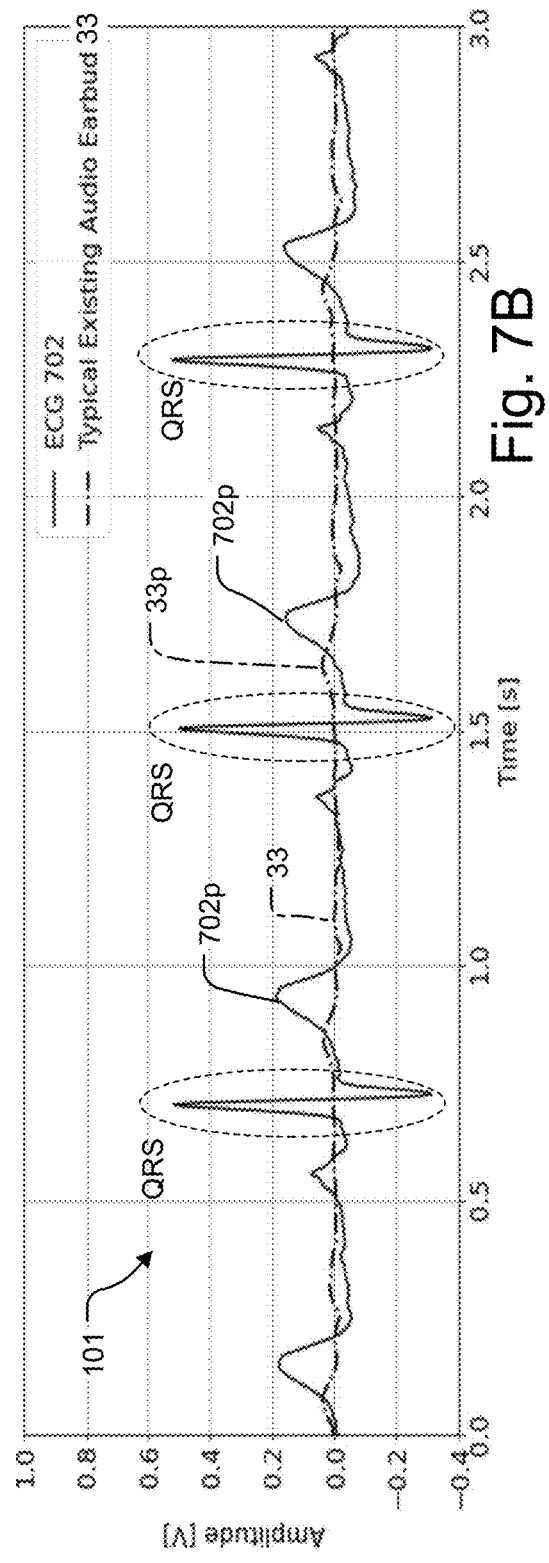

VIBROACOUSTIC EARBUD

RELATED APPLICATIONS

This application is a continuation of U.S. patent application Ser. No. 17/843,926 filed on Jun. 17, 2022, which claims the benefit under 35 USC 119 (e) of U.S. Provisional Application No. 63/212,570 filed on Jun. 18, 2021, all of which are incorporated herein by reference in their entireties.

BACKGROUND OF THE INVENTION

Audio earbuds are devices which are worn at or near an ear canal of individuals. These existing earbuds include speakers and microphones that generally both operate in the audible range. The audio earbuds are either wired or wireless.

The audio earbuds are typically in communication with one or more applications ("apps") executing on user devices carried by the individuals. In one example, a music app executing on a mobile phone user device sends audible sounds to the speakers of the existing audio earbuds for presentation at the ear canals of the individual. In another example, the microphones detect audible sounds from the body of the individual in the ear canals, and send electronic representations of the audible sounds to a heart rate monitor app executing on the mobile phone. The heart rate monitor app then presents the representations of audible sounds on a display screen of the mobile phone so that the individuals can track their heart rate.

More recently, earbuds including sensors that can detect infrasounds and audible sounds have been introduced. These infrasonic earbuds also include speakers that can present audible sound for playback at the ear canals of the individuals. See U.S. Pat. No. 11,234,069 (hereinafter "the '069 patent") with issue date of Jan. 25, 2022.

SUMMARY OF THE INVENTION

On occasion, earbuds can exhibit unintentional leaks. These unintentional leaks occur when a normally snug fit between the earbuds and the ear canals are disrupted. This disruption can be caused by movement of the individual such as stretching or walking, or an initial fit that loosens over time. The leaks cause acoustic pressure in the ear canals to decrease, which correspondingly decreases the amplitude of infrasounds from the body of the individual that the earbuds can detect in the ear canals.

A novel vibroacoustic earbud ("earbud") is proposed. The earbud is substantially the same as the infrasonic earbud described in the '069 patent with the modifications described herein. The contents of the '069 patent are incorporated by reference in its entirety.

The earbud includes a housing and an infrasonic/vibration sensor. The housing includes a nozzle that is configured for positioning within an ear canal of an individual. The sensor is included within the nozzle and detects biosignals including infrasonic signals from a body of the individual in the ear canal.

The nozzle is constructed or otherwise formed to include a nozzle tip that inserts into the individual's ear canal and engages with a wall of the ear canal to provide an earbud seal. Additionally or alternatively, a separate earbud tip can attach to the nozzle and engage with the wall of the ear canal to form the nozzle tip that provides the earbud seal.

The earbud seal allows acoustic pressure to build in the ear canal, the result of which forms an ear canal acoustic volume that amplifies the biosignals. The earbud is tuned to minimize loss of amplitude of the biosignals when an unintentional leak occurs in the earbud seal that possibly reduces acoustic pressure in the ear canal acoustic volume.

During the design phase, the earbud is tuned by making physical changes to the earbud to maximize biosignal amplitude in the ear canal acoustic volume in the presence of unintentional leaks of the earbud seal. The earbud is then constructed using the fixed design. In one example, different versions of the earbud can be constructed based upon different anticipated leak levels of the earbud seal.

In general, according to one aspect, the invention features a vibroacoustic earbud ("earbud"), comprising a housing and a nozzle tip. The housing includes a nozzle that is configured for positioning within an ear canal of an individual, and an infrasonic/vibration sensor included within the nozzle that detects biosignals including infrasonic signals from a body of the individual in the ear canal. The nozzle tip engages with a wall of the ear canal to create an earbud seal, forming an ear canal acoustic volume that amplifies the biosignals in the ear canal. Due to an unintentional leak that occurs in the earbud seal that possibly reduces an acoustic pressure in the ear canal acoustic volume, the earbud is tuned to minimize loss of amplitude of the biosignals detected by the sensor in the ear canal acoustic volume.

In one implementation, the earbud is tuned to limit a low frequency biosignal roll off in a biosignal transfer function of the earbud. The biosignal transfer function relates an acoustic pressure at the infrasonic/vibration sensor to the acoustic pressure in the ear canal acoustic volume, where the acoustic pressure in the ear canal acoustic volume is produced by the biosignals.

Preferably, the low frequency biosignal roll off is between −15 dB and 0 dB at 1 Hz. Typically, a −3 dB frequency of the low frequency biosignal roll off is approximately 3 Hz, and the low frequency biosignal roll off drops no more than approximately 3 dB between 3 Hz and 1 Hz.

In another implementation, the earbud includes a speaker within the housing, and the earbud is tuned by selecting a speaker with a speaker effective acoustic volume that is less than or equal to ½ that of the ear canal acoustic volume.

The earbud can also be tuned to limit an audio signal roll off in an audio transfer function of the earbud. The audio transfer function relates a voltage driving the speaker to the acoustic pressure in the ear canal acoustic volume, where the acoustic pressure in the ear canal acoustic volume is produced by audio signals presented at the ear canal by the speaker. Preferably, the audio signal roll off is between −15 dB and 0 dB at 1 Hz. Typically, a −3 dB frequency of the audio roll off is approximately 3 Hz, and the audio roll off drops no more than approximately 3 dB between 3 Hz and 1 Hz.

In yet another implementation, the earbud includes a rear housing portion and a front housing portion, and an internal tuned port located between the rear housing portion and the front housing portion. The earbud is tuned by constructing the internal tuned port and the nozzle to each provide intentional leaks within the earbud such that the intentional leak provided by the internal tuned port relative to the intentional leak provided by the nozzle is in a range of ratios between 1:1 and 4:1.

In still another implementation, the earbud is tuned to provide an overall intentional leak within the earbud, the value of which is on the order of the unintentional leak.

In general, according to another aspect, the invention features a vibroacoustic earbud ("earbud") method. The method comprises: positioning a nozzle of a housing of the earbud within an ear canal of an individual, and an infrasonic/vibration sensor included within the nozzle detecting biosignals including infrasonic signals from a body of the individual in the ear canal; and engaging a nozzle tip of the nozzle with a wall of the ear canal to create an earbud seal, forming an ear canal acoustic volume that amplifies the biosignals in the ear canal. The earbud is tuned to minimize loss of amplitude of the biosignals detected in the ear canal acoustic volume by the sensor, the loss of amplitude of the biosignals being the result of an unintentional leak occurring in the earbud seal that possibly reduces acoustic pressure in the ear canal acoustic volume.

In one implementation, the earbud is tuned to minimize loss of amplitude of the biosignals detected in the ear canal by locating an internal tuned port between a rear housing portion and a front housing portion of the earbud, and constructing the internal tuned port and the nozzle to each provide intentional leaks within the earbud such that the intentional leak provided by the internal tuned port relative to the intentional leak provided by the nozzle is in a range of ratios between 1:1 and 4:1.

In general, according to yet another aspect, the invention features a vibroacoustic apparatus. The vibroacoustic apparatus includes a housing having an interior and a nozzle configured to be positioned within an ear canal of an individual during use, where the nozzle forms a nozzle opening configured to receive infrasonic and non-infrasonic signals and the housing defines a front acoustic volume and a rear acoustic volume. The vibroacoustic apparatus also includes an infrasonic/vibration sensor within the nozzle that is configured to detect biosignals including infrasonic biosignals from the body of the individual, and includes a plurality of additional openings through the housing that together provide a fluid pathway from the rear acoustic volume to the front acoustic volume and into the ear canal via the nozzle opening.

In more detail, the nozzle is also configured to form a seal around the nozzle with the ear canal during use that allows acoustic pressure to increase in the ear canal. The fluid pathway is configured to form an acoustic leak that contributes to the acoustic pressure within the ear canal during use, and the fluid pathway is configured to control the ear canal acoustic pressure to at least in part offset a leak in the seal to enhance a fidelity of the infrasonic biosignals.

The vibroacoustic apparatus can include an acoustic resistor coupled with at least one of the additional openings. Additionally, the plurality of additional openings might include a front opening fluidly connecting the front acoustic volume with the interior, and a back opening fluidly connecting the rear acoustic volume with the interior.

Additionally, the plurality of additional openings might include an internal opening fluidly connecting the front acoustic volume with the rear acoustic volume, where an acoustic leak provided by the internal opening relative to an acoustic leak provided by the nozzle is in a range of ratios between 1:1 and 4:1.

In one example, the vibroacoustic apparatus preferably has an associated audio transfer function with a roll off between −15 dB and 0 dB at 1 Hz. Typically, the roll off between 10 Hz and 1 Hz has a negative slope of no greater than 5 dB.

In another example, the vibroacoustic apparatus preferably has an associated biosignal transfer function with a roll off between −15 dB and 0 dB at 1 Hz. Typically, a −3 dB frequency of the roll off is approximately 3 Hz, and the roll off between 3 Hz and 1 Hz has a negative slope of no greater than 3 dB.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 7A shows time-domain amplitude plots of biosignals obtained from an exemplary proposed earbud and from an electrocardiogram (ECG) for the same individual, over the same time frame;

FIG. 7B show time-domain amplitude plots of biosignals obtained from a typical existing audio earbud and from an ECG for the same individual, over the same time frame.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
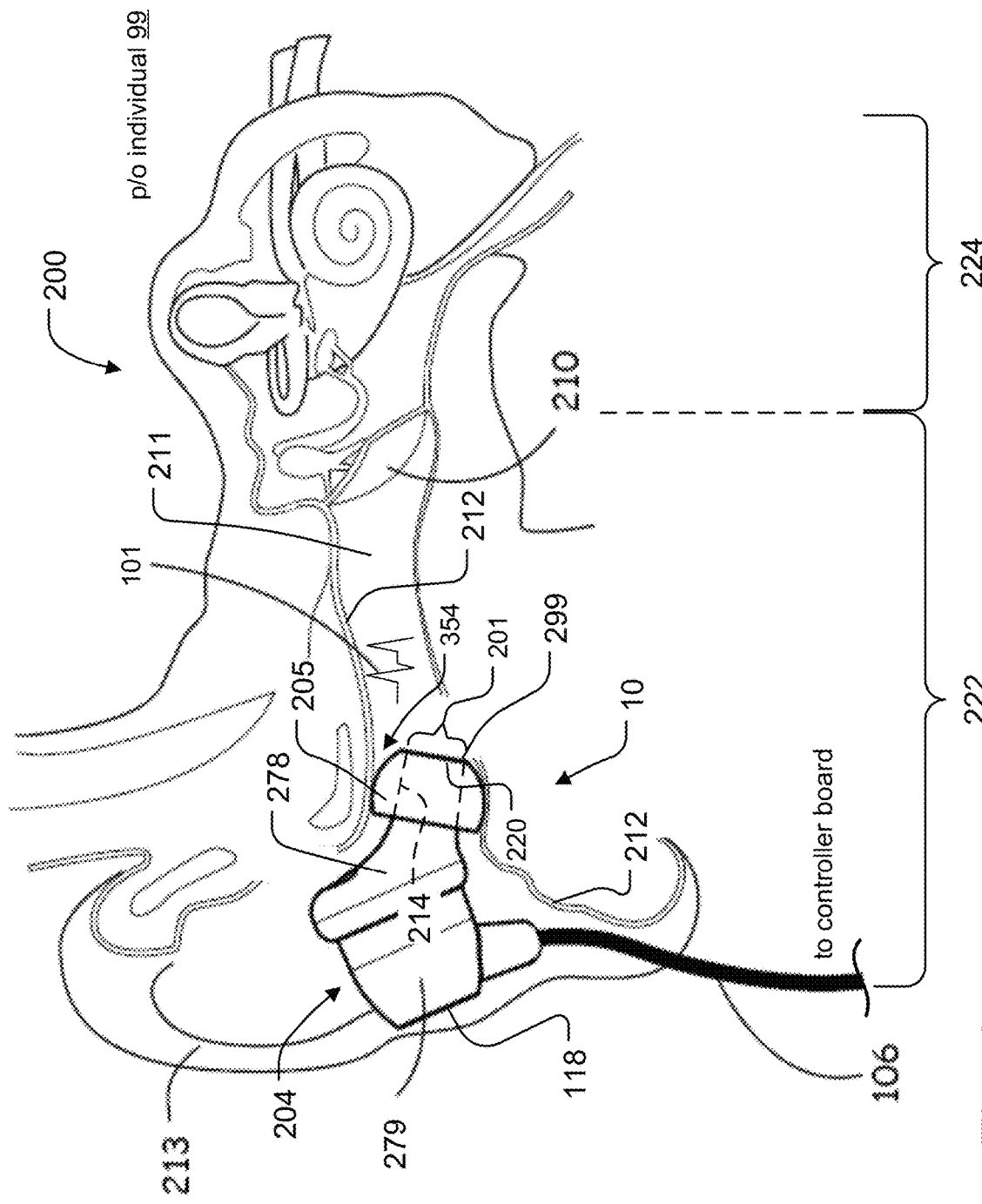
FIG. 1 is a cross-sectional anatomical depiction of an individual's ear, where a proposed vibroacoustic earbud ("earbud") is placed at/within an ear canal of the individual, and where the earbud includes an infrasound/vibration sensor that may detect both infrasonic and audible signals in the ear canal.

FIG. 1 is an exemplary vibroacoustic earbud ("earbud" 10) placed within an ear 200 of an individual 99. The earbud 10 is an acoustical device that is designed to seat within/at an outer portion of an ear canal of the ear 200.

The ear 200 has an external portion 222 and an inner portion 224. Relevant portions of the external portion 222 include a pinna 213, an ear canal 211 and a tympanic membrane 210. Only one earbud 10 placed within a right ear 200 of the individual 99 is shown. Another earbud 10 can also be placed into a left ear 200 of the individual 99.

The earbud 10 includes various components. These components include a housing 204, a nozzle 214 (shown in phantom), a nozzle tip 205 and an earbud connection 106. Here, the nozzle tip 205 is in the form of a separate earbud tip attached to the nozzle 214.

More detail for the components of the earbud 10 is as follows. The housing 204 includes a front portion 278 and a rear portion 279. The front housing portion 278 faces the ear canal 211 and the rear housing portion 279 faces outward away from the pinna 213. The rear housing portion 279 has a distal end 118 that faces away from the pinna 213. The front and rear housing portions 278, 279 can be separate pieces of material such as lightweight plastic that are attached to one another, or can be formed from the same piece of material.

The nozzle 214 is shown in phantom. The nozzle 214 has a proximal end 220 and a nozzle opening 201 at its proximate end 220. The nozzle 214 can be a separate piece fitted to the front housing portion 278 or can be formed as part of the front housing portion 278, in examples. Generally, the proximal end 220 of the nozzle 214 is cylindrical in shape, and the housing 204 is spherical in shape. However, other shapes for the nozzle 214 and the housing 204 are possible.

The nozzle tip 205 has an opening that coincides with the nozzle opening and has a face 299 that is configured for placement in the ear canal 211. When the nozzle tip 205 is implemented as a separate earbud tip, as shown, the tip attaches to the proximal end 220 of the nozzle 214.

The earbud connection 106, as shown, is a cable that includes multiple wires that electrically connect the earbud 10 to a computer controller board (not shown). Some of the wires of the earbud connection 106 enable the transfer of control and data signals between the earbud 10 and the controller board. Other wires provide power to the earbuds 10. In one implementation, the housing 204 of each earbud 10 includes a battery that provides a local source of power to each earbud 10. In another implementation, the housing 204 of one earbud 10 includes a battery that provides a local source of power to one or both earbuds 10.

In another implementation, the earbud connection 106 is a wireless connection. In this example, the earbuds 10 each include a local battery and a wireless earbud transceiver that communicates with a wireless transceiver of the controller board. The battery provides a source of power to the components within each earbud including the earbud transceiver. The earbud transceiver then communicates the data and control signals over one or more wireless links to the wireless transceiver of the controller board. In yet another implementation, the controller board is incorporated within one or both earbuds.

The individual 99 inserts the earbud 10 into the ear 200 by placing the face 299 of the nozzle tip 205 into the ear canal 211. The face 299 engages with a wall 212 of the ear canal 211 to provide an earbud seal 354. The earbud seal 354 isolates the ear canal 211 from outside air and from sounds originating externally to the earbud 10. When the earbud seal 354 is applied to the ear canal 211, the ear canal is also referred to as an occluded ear canal.

The housing 204 also rests against the pinna 213. The nozzle tip 205 and the pinna 213 thus support the earbud 10 in the individual's ear 200.

In one implementation, as shown, the components of the earbud 10 are typically arranged as follows. The front housing portion 278 is separate from and attaches to the rear housing portion 279 with acoustically-insulating sealant. The nozzle 214 is formed as part of the front housing portion 278. The separate earbud tip that forms the nozzle tip 205 attaches to the nozzle 214 at the proximal end 220 of the nozzle 214. One end of the earbud cable 106 attaches to the housing 204 at its rear housing portion 279, while the other end of the cable 106 attaches to the computer controller board (not shown).

Infrasounds

Biosignals such as acoustic signals are generated internally in the body of the individual 99 by breathing, heartbeat, coughing, muscle movement, swallowing, chewing, body motion, sneezing and blood flow, in examples. The acoustic signals can be also generated by external sources, such as air conditioning systems, vehicle interiors, various industrial processes, etc. The acoustic signals include audible and infrasonic signals.

The acoustic signals represent tiny fluctuating pressure changes superimposed on the normal ambient pressure of the individual's body and can be defined by their spectral frequency components. Sounds with frequencies ranging from 20 Hz to 20 kHz represent those typically heard by humans and are designated as falling within the audible range ("audible sounds"/"audible signals"). Sounds with frequencies below the audible range (i.e., from 0 Hz to 20 Hz) are infrasonic or infrasounds. For example, the average heart rate of a healthy individual is 60 beats per minute (bpm), which corresponds to a frequency of 1 Hz. (1 cycle/second).

The level of a sound is normally defined in terms of the magnitude of the acoustic pressure changes it represents. These changes can be measured and may depend on the frequency of the sound. Typical levels of sound pressure in air are five magnitudes of order less than ambient pressure conditions.

Roll off is a characteristic of the frequency response plot/transfer function of acoustical devices. Acoustical devices are typically designed to reproduce acoustic signals better (i.e., with higher gain) at some frequencies than others. Usually, the gain is high and fairly consistent/has a near-zero slope over a range of frequencies that the device can reproduce well. The gain then increasingly "drops off" with an increasingly negative slope over a range of frequencies that the device cannot reproduce as well (or at all). In the transfer function, the frequency portion of the plot where the gain drops off with an increasingly negative slope is also known as the roll off. The roll off is characterized by the frequency value at which the drop off in gain is at least-3 decibels (dB), and by the slope of the roll off.

By way of background, the human body generates mechanical vibrations and/or acoustic waves that travel through different media in the body such as the blood vessels, bones, muscles, tissue and cartilage. Such vibrations produced by the human body may be sensed by different transducers and/or vibration sensors attached at different parts of the body, for example, as in seismocardiography and ballistocardiography. The earbuds 10 detect these mechanical vibrations and/or acoustic waves via one or more sensors included within the earbud 10.

Because the nozzle tips 205 of the earbuds 10 seal the opening to the ear canal 211, acoustic pressure inside the ear canal can build up/increase, and the body vibrations can be trapped inside the ear canal 211 and possibly also within the earbud 10. This increase in acoustic pressure can amplify the vibrations, especially the low frequency infrasound vibrations/infrasounds described herein above. This relationship may be characterized by the following equation:

$Za = P/Va$, where

P=Acoustic pressure within the ear canal, in Pascals
Va=Acoustic volume velocity of the air in the ear canal, in cubic meters per second (m3/sec)

and

Za=Acoustic impedance measured from the ear canal outwards toward free space, measured in units of Pascal-seconds per cubic meter (Pa*sec/m3).

By way of example, human body vibrations associated with the cardiovascular system of the individual 99 may be generated in the frequency range 0-25 Hertz (Hz), with a majority of the signal in the range of 0 to 5 Hz. Such vibrations have a wavelength varying from 13 meters (m) to 3.3 kilometers (km0 in air, at about 20 degrees Centigrade (20 C). The wavelengths of infrasounds are considerably longer than the length of any ear dimension, and as a result are relatively low frequencies.

At low frequencies, the acoustic impedance measured at/associated with an open ear canal 211 is negligible. However, as the ear canal 211 is occluded and sealed from outside air, the acoustic impedance of the ear canal increases with decreasing ear canal volume.

In general, the impedance of a sealed cavity such as the sealed ear canal 211 can be expressed as $Zcavity \sim (p^*C2)/Volume$, where Zcavity=Acoustic impedance of a sealed cavity
p=the density of air (1.21 kg/m3)
C=the speed of sound in air (~342 m/sec), and
Volume=the volume of the cavity, in cubic meters (m3).

As the volume of the ear canal 211 decreases with insertion of the nozzle tip into the ear canal 211, due to the earbud seal 354, the impedance of the ear canal cavity, Za, increases. As a result, for a given volume velocity Va caused by the body, the acoustic pressure will increase relative to the acoustic pressure in the unoccluded ear canal 211. It is important to note that acoustic pressures are very, very small compared to normal atmospheric conditions so the effect is not noticed by the individual.

As an additional non-limiting example, one form of the ideal gas law states that $P1^*V1 = P2^*V2$, where P1=Initial body-generated acoustic pressure in the unoccluded ear canal, in Pascals (Pa)
V1=Initial volume of the unoccluded ear canal, in m3
P2=Acoustic pressure in the occluded ear canal, in Pa
V2=Volume of the occluded ear canal, in m3

The volume of the unoccluded ear canal 211 is quite large. This volume approaches infinity when measured from the ear canal 211 towards the pinna 213 and outward into free space. In contrast, the volume of the occluded ear canal 211 for a typical adult is on the order of 2 cubic centimeters (cc). The large decrease in volume from the initial, unoccluded ear canal volume V1 to the occluded volume V2 correspondingly causes a large increase in the acoustic pressure of the ear canal from P1 to P2. By way of example, a decrease in volume from 200 cc to 2 cc would increase the acoustic pressure in the ear canal 211 by 40 dB.

Figure 2:
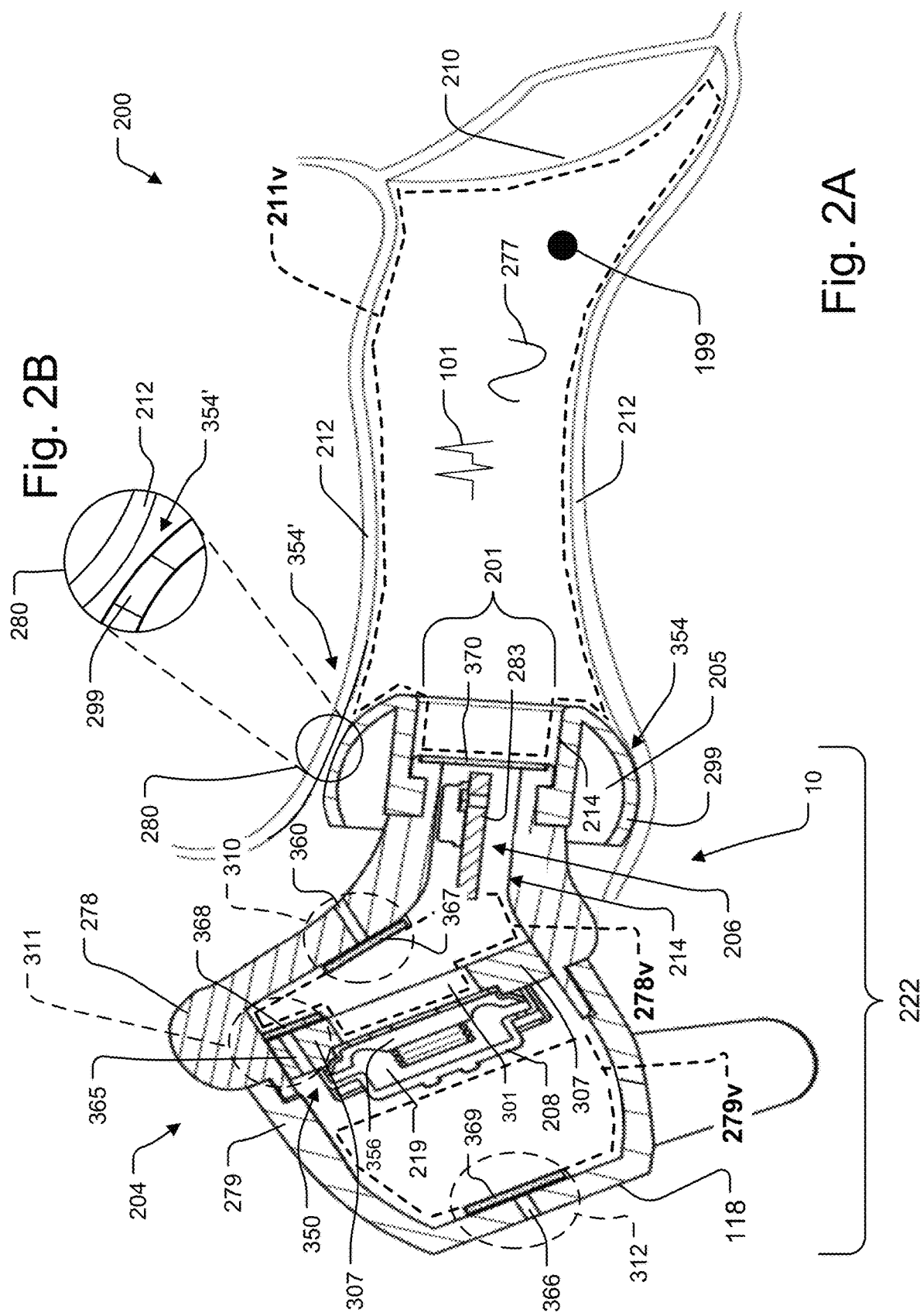
FIG. 2A is a cutaway view of the earbud in FIG. 1, showing components of the earbud and positioning of the earbud relative to the ear canal, according to an embodiment, where a speaker of the earbud that presents audible signals at the ear canal is also shown.
FIG. 2B is a magnified inset view of a selected portion in FIG. 2A, where the view shows more detail for how a nozzle tip of the earbud is designed to form an airtight seal against a wall of the ear canal, and shows how the seal can become less than airtight and cause an unintentional leak, due to improper earbud fit or motion of the individual, in examples.

FIG. 2A shows a preferred embodiment of an earbud 10. In the illustrated example, the earbud 10 is positioned at/within the external portion 222 of the ear 200 of the individual 99. The earbud 10 and the external portion 222 are shown in cross-section to show components of/within the earbud 10, and to enable description of the components with respect to the external portion 222. To facilitate the illustration and description of the earbud 10, the pinna 213 and the earbud cable 106 are not shown.

The earbud 10 includes various components within the housing 204 and/or nozzle 214 that could not be shown in FIG. 1. These components include a speaker 208, an acoustic sensor such as an infrasonic/vibration sensor 206 and multiple tuned ports. Additional components may include other sensors including a pressure sensor, a motion sensor and possibly even a temperature sensor (not shown). In addition, a front acoustic volume 278*v*, a rear acoustic volume 279*v*, and an ear canal acoustic volume 211*v* are shown.

The speaker 208 is included within the rear housing portion 279 and includes a back portion 219 and a diaphragm 356. The speaker 208 also includes a speaker ring 307 that provides an airtight speaker seal 350 between the front and rear housing portions 278, 279. In other examples, the speaker ring 307 might be integrated into other components of the earbud, or might be provided using adhesive or gasketing. Regardless of its physical form or implementation, the speaker ring 307 divides the front housing portion 278 from the rear housing portion 279 with a seal around the speaker 208. The diaphragm 356 faces an opening 301 between the front and rear housing portions and presents audible signals 277 to the ear canal 211, via the nozzle 214 and the nozzle opening 201. The back portion 219 is located behind the diaphragm 356 and faces the rear housing portion 279.

The speaker seal 350 also enables a rear acoustic volume 279*v* to form in the rear housing portion 279 and a front acoustic volume 278*v* to form in the front housing portion 278 during operation of the earbud 10. The front acoustic volume 278*v* is formed in a space between the diaphragm 356 and the nozzle 214. The rear acoustic volume 279*v* is formed in an area of the rear housing portion 279 behind the speaker ring 307.

The speaker 208 can be any type of electroacoustic transducer common for audio earbud applications, including dynamic, electrostatic, and balanced armature speakers. The motion sensor might be an accelerometer, a gyroscope, or a combination of these devices. The pressure sensor, the temperature sensor and the motion sensor are not shown in the figure.

The earbud seal 354 is formed between the face 299 of the nozzle tip 205 and the wall 212 of the ear canal 211. To provide this seal 354, the tip 205 is generally spherical in shape and is formed from a pliable material that enables a snug fit of the tip 205 in the ear canal 211. The material might be silicone, foam such as memory or acoustical foam, or rubber, in examples. As noted hereinabove, the nozzle tip 205 might also be integrated with the nozzle 214 rather than being a separate component that attaches to the proximal end 220 of the nozzle 214. In this way, the nozzle 214 is suspended within the ear canal 211 when the nozzle tip 205 is engaged with the ear canal 211/wall 212 of the ear canal 211.

When the nozzle tip 205 is a separate earbud tip that attaches to the nozzle 214, the nozzle tip typically attaches using a fit such as a press fit or a friction fit. This allows the nozzle tips to be replaced over time, and allows different sized tips for different ear canal sizes, in examples.

The earbud seal 354 provides the following benefits. First, it prevents air from entering the ear canal 211, and can significantly attenuate external sounds that might otherwise interfere with the biosignals 101. The seal 354 also enables acoustic pressure to build up/increase within the ear canal 211. This seal 354 forms the ear canal acoustic volume 211*v* and can significantly amplify/increase the amplitude of the biosignals 101 from the body of the individual 99 that enter the ear canal 211. At the same time, this acoustic pressure increase is also harmless to the individual 99.

The material of the nozzle tip 205 also impacts the earbud seal 354 and the ability of the earbud 10 to detect the biosignals 101. During operation of each earbud 10, the biosignals 101 within the ear canal 211 strike the nozzle tip 205, causing the tip 205 to vibrate. If the material that forms the nozzle tip 205 is too compliant, the nozzle tip 205 might vibrate enough to modulate the acoustic volume 211*v* which may in turn modulate the acoustic pressure within the ear canal in undesirable ways. As a result, a more rigid/acoustically stiff material is typically selected for the nozzle tip 205 to minimize the vibrations of the nozzle tip 205, and thus to maximize the earbud seal 354. The maximizing of the earbud seal 354 constrains the ear canal acoustic volume 211*v* and thus maximizes the amplitude of the biosignals 101 in the ear canal acoustic volume 211*v* that the infrasonic/vibration sensor 206 can detect.

On occasion, the earbud seal 354 can become less than airtight. This is indicated by reference 354' and is also known as an unintended or unintentional leak. In examples, this unintentional leak can occur when the fit of the nozzle tip 205 in the ear canal 211 is not snug against the wall 212 when initially inserted, or when the nozzle tip 205 moves away from a portion of the wall 212 due to motion of the individual 99.

With an in-ear (intra-concha) earbud design such as the illustrated earbud 10, the dominant acoustic leak that affects low-frequency behavior is the inside-to-outside unintentional leak 354'. If the earbud fit is very tight, there is a negligible amount of unintentional leak 354' and thus very strong reproduction of low frequency sounds (especially infrasounds) results. If the fit is too loose, the unintentional leak 354' can be large, and weak low frequency sound reproduction results.

Because of the possibility of the unintentional leak 354', the earbud 10 is designed to provide an overall intentional leak, the value of which is on the order of the unintentional leak 354'. The intentional leak is designed to reduce the variance in sound reproduction performance of the earbud 10 for different levels of the earbud seal 354/different levels of the unintentional leak 354'. In this way, the frequency response of the earbud 10 is more consistent across a large range of individuals 99 with different geometries of ear canals 211 and different levels of earbud fit.

To provide more detail for the unintentional leak 354', a portion of the inner ear canal where the unintentional leak 354' occurs is highlighted as an inset view in FIG. 2B and indicated by reference 280. More detail for the inset view 280 is provided in the description that accompanies FIG. 2B, included herein below.

The nozzle 214 includes the infrasonic/vibration sensor 206 and the pressure sensor (not shown). The infrasonic/vibration sensor 206 is preferably located at the proximal end 220 of the nozzle 214 and attaches to an inside wall of the nozzle 214. The infrasonic/vibration sensor 206 has a detection face 283 that receives and detects the biosignals 101 that enter the nozzle 214 via the nozzle opening 201.

The nozzle 214 also includes a nozzle resistor 370. The nozzle resistor is an acoustic resistor which minimizes the ingress of particles, such as ear wax, into the nozzle 214. The nozzle resistor 370 also limits the possibility of damage to the infrasound/vibration sensor 206. The nozzle resistor 370 is configured so that it does not negatively affect low-frequency audio performance or biosignal 101 acquisition. The nozzle resistor 370 is a finely perforated membrane made of cloth, foam, or otherwise dissipative material.

The earbud 10 also includes at least one tuned port. In the illustrated example, the earbud 10 includes a front tuned port 310, an internal tuned port 311 and a rear tuned port 312. Each tuned port includes a port tube (i.e., an opening)

formed in the housing 204 and an acoustic resistor disposed on the port tube. Each tuned port is tuned, as part of construction/configuration of the earbud 10, to minimize variation of amplitude of the biosignals 101 in the ear canal acoustic volume 211v when an unintentional leak 354' occurs in the earbud seal 354 that possibly reduces the pressure in the ear canal 211. This variation is present across units of earbuds 10, instances of earbud seals 354, and users' ear canals 211.

The one or more tuned ports 310-312 and/or the nozzle 214 are configured to tune the earbud 10 for optimal quality and amplitude of the biosignals 101, and for optimal quality and amplitude of the audible signals 277 in the ear canal acoustic volume 211v. The tuned ports 310-312 and/or the nozzle 214 are also configured for sufficient comfort of the individual 99. The tuned ports 310-312 and/or the nozzle 214 also mitigate the effect of any unintentional leak 354' upon the earbud 10 during its operation.

The front tuned port 310 includes a front port tube 360 and a front acoustic resistor 367 and acoustically couples the front acoustic volume 278v to the outside world/free space. The front port tube 360 is formed in the front housing portion 278. The acoustic resistor 367 is disposed on the front port tube 360 and is included within the front housing portion 278.

The internal tuned port 311 includes an internal port tube 365 and an internal acoustic resistor 368. The internal port tube 365 is formed within the housing 204 at a location where the front and rear housing portions 278, 279 attach and provides a pathway between the portions 278, 279. The internal tuned port 311 acoustically couples the front acoustic volume 278v and to the rear acoustic volume 279v. For this purpose, in one implementation, the internal tuned port 311 passes through a portion of the speaker seal 307. The internal acoustic resistor 368 is disposed on the internal port tube 365 and is included within the front housing portion 278.

The rear tuned port 312 includes a rear port tube 366 and a rear acoustic resistor 369 and acoustically couples the rear acoustic volume 279v to the outside world/to free space. The rear port tube 366 is formed within the rear housing portion 279, typically at the distal end 118 of the rear housing portion 279. The rear acoustic resistor 369 is disposed on the rear port tube 366 and is included within the rear housing portion 279.

The acoustic resistors of the tuned ports 310-312 and the nozzle 214 have the following properties. Each acoustic resistor 367, 368, 369, and 370 is a finely perforated membrane made of cloth, foam, or otherwise dissipative material and is acoustically coupled to its respective tuned port tube 360, 365, 366 and nozzle 214. Additionally or alternatively, one or more of the acoustic resistors might be attached to the outside of the housing 204, such that they are disposed against their respective port tubes at the outside of the housing 204.

The earbud 10 generally operates as follows. Biosignals 101 including infrasonic signals from the body of the individual 99 exit the body via the wall 212 and enter the ear canal 211. Once the earbud 10 is inserted in the ear canal 211 and the face 299 of the nozzle tip 205 engages with the wall 212, the earbud seal 354 forms. The earbud seal 354 enables the acoustic pressure in the ear canal 211 to increase and thus decreases the ear canal acoustic volume 211v. The decrease in the ear canal acoustic volume 211v correspondingly increases the amplitude of the biosignals 101 that enter the ear canal acoustic volume 211v.

Prior to insertion of the earbud 10, the initial acoustic pressure in the ear canal is approximately zero. Once the earbud 10 is inserted and the earbud seal 354 is sufficient, the acoustic pressure in the ear canal 211 rises to a detectable level, indicated by reference 199.

The biosignals 101 from the body of the individual 99 enter the ear canal/the ear canal acoustic volume 211v, and then enter the nozzle opening 201/opening of the nozzle tip 205 and propagate within the nozzle 214. The biosignals 101 impinge upon the detection face 283 of the infrasonic/vibration sensor 206, and the sensor 206 sends an electronic representation of the detected biosignals 101 via the earbud connector 106 to the controller board. The controller board buffers and sends the electronic representation of the biosignals 101 to one or more computer systems for analysis and reporting.

At the same time, the speaker 208 can receive electrical signals from an audio source. The diaphragm 356 presents the electrical signals as sound waves (the audible signals 277) into the ear canal 211 via the nozzle 214. The tympanic membrane 210 then vibrates in response to the audible signals 277.

The one or more tuned ports 310-312 and/or the nozzle 214 can then mitigate the effects of the unintentional leak 354' upon the ability of the earbud 10 to reproduce the audible signals 277 and to detect the biosignals 101 in the ear canal acoustic volume 211v. More detail for the operation of each tuned port follows below.

At the internal tuned port 311, the internal port tube 365 introduces an intentional acoustic leak in the speaker seal 350. This provides a pathway for air to be shared between the front and rear housing portions 278, 279. The introduction of the intentional leak couples the pressure in the front and rear acoustic volumes 278v, 279v, the result of which correspondingly affects the pressure in the ear canal acoustic volume 211v. This is intended to bound any pressure loss in the ear canal acoustic volume 211v due to the unintentional leak 354', which affects both audible signal 277 performance/reproduction and biosignal 101 acquisition of the earbud 10. The introduction of the intentional leak also reduces variability in the audible signals 277 and the biosignals 101 over time, across a population of different types and sizes of manufactured earbuds 10. The effect of the leak introduced by the internal port 365 can be regulated by selection of the internal acoustic resistor 368, in one example.

At the rear tuned port 312, the rear port tube 366 introduces an "inside to outside" intentional acoustic leak that causes a release of acoustic pressure from the rear housing portion 279 to the outside air. This intentional leak is intended to extend the audio response of the speaker 208 such that the audible signals 277 it reproduces extend to a lower frequency range. If the rear port tube 366 is very small/provides a narrow opening or is otherwise highly resistive, then the rear port tube 366 has less of an effect on the biosignal 101 than it does on the audio performance (i.e., upon the audible signals 277).

However, if the opening of the rear port tube 366 is too large, it correspondingly increases/raises the low cut off frequency of the rear acoustic volume 279v. This increase in the low cut off frequency of the rear acoustic volume 279v, which when coupled to the other acoustic loads in the system results in a decrease in the response of the infrasonic/vibration sensor 206 to the biosignals 101 which are primarily observed at low frequencies. The effect of the rear port tube 366 can be regulated by selection of the rear acoustic resistor 369, in one example.

As a result, the earbud 10 can form an vibroacoustic apparatus that includes an acoustic resistor coupled with at least one of the openings/port tubes 360, 365, 366. In examples, the front port tube 360 fluidly connects the front acoustic volume 278v with the interior of the housing 204, and the rear port tube 366 fluidly connects the rear acoustic volume 279v with the interior of the housing 204.

In FIG. 2B, the inset view 280 of FIG. 2A is magnified to show more detail for the unintentional leak 354'. The unintentional leak 354' is characterized by a less than airtight seal between the wall 212 and the face 299 of the nozzle tip 205. If the amount of the unintentional leak 354' is significant, the acoustic pressure in the ear canal 211 can drop to a level that can materially impact the signal quality and amplitude of the biosignals 101 detected by the infrasound/vibration sensor 206.

Figure 3:
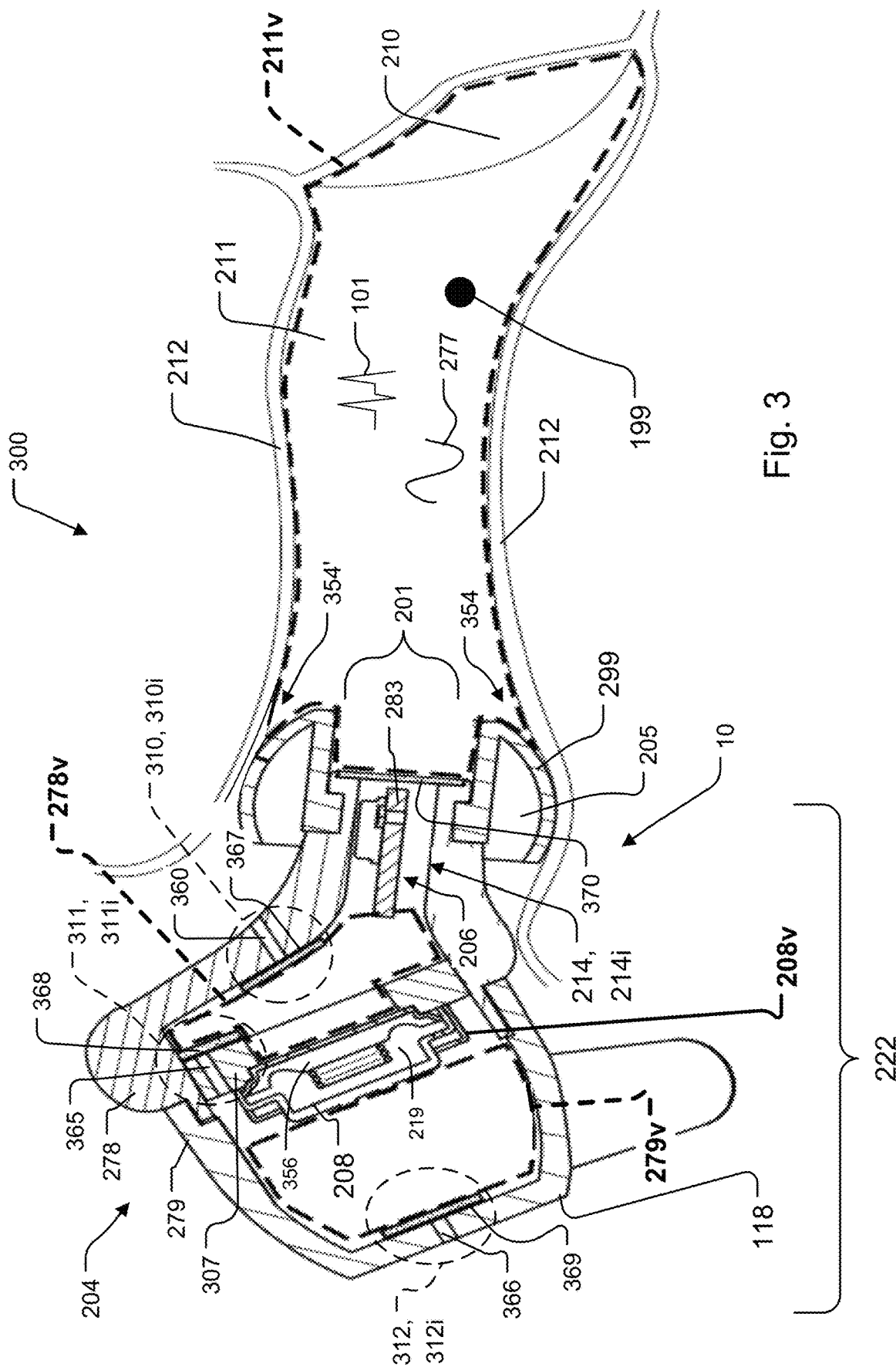
FIG. 3 is a cutaway view of the earbud in FIG. 1, where the figure illustrates a mechano-acoustical system formed during operation of the earbud.

FIG. 3 illustrates a mechano-acoustical system 300 formed by the earbud 10 in response to operation of the earbud 10. The mechano-acoustical system 300 represents an acoustic equivalent of the earbud 10 and is another way of describing the operation of the earbud 10.

The mechano-acoustical system 300 includes various acoustical components. The acoustical components model various physical components of the earbud 10 or otherwise represent the physical components in the mechano-acoustical system 300. These acoustical components include acoustic volumes, acoustic impedances, acoustic resistances and acoustic masses, in examples.

The acoustic volume of the overall earbud 10 is a sum of individual effective acoustic volumes of components within the earbud 10, and acoustic volumes formed in spaces/cavities within the housing 204 through which sound can propagate. These acoustic volumes include a speaker effective acoustic volume 208v, the front acoustic volume 278v and the rear acoustic volume 279v. The speaker effective acoustic volume 208v is an intrinsic property of the speaker 208 and accounts for the acoustic volume produced by the operation of the speaker 208 at its installed location in the housing 204, and includes the stiffness and mass of the diaphragm 356 and the motor mechanics of the speaker.

The acoustic impedance of the earbud 10 is a sum of individual acoustic impedances of components within the earbud 10. These acoustic impedances include a nozzle impedance 214i, and impedances for the tuned ports including a front tuned port impedance 310i, an internal tuned port impedance 311i and a rear tuned port impedance 312i.

More detail for the tuned port impedances 310i-312i is as follows. The impedance of each port is a complex number with a real and an imaginary part. Each tuned port has an effective acoustical mass (imaginary part) and an effective acoustical resistance (real part). The tuned port tube (specifically, its opening and length) and the acoustic resistor each have an acoustical resistance, the sum of which is the effective acoustical resistance of the tuned port. The tuned port also has an acoustical mass, which is the effective mass of the tuned port. Thus, the impedance of each tuned port is the sum of its effective acoustical mass and its effective acoustical resistance.

The nozzle 214 can be modeled in the acoustic domain as a tuned port and thus has a nozzle impedance 214i. This is because the nozzle 214 is effectively a port tube, where the nozzle opening 201 extends into the nozzle 214 along its entire length. As with the tuned ports 310-312, the nozzle 214 (specifically, the nozzle opening 201) and the nozzle acoustic resistor 370 each have an acoustical resistance, the sum of which is the effective resistance of the nozzle 214. The nozzle 214 also has an acoustical mass, which is the effective mass of the nozzle 214. Thus, the nozzle impedance 214i is the sum of its effective acoustical mass and its effective acoustical resistance.

Adjustments to the lengths and/or openings of the port tubes and resistors of the tuned ports 310-312 can change the impedances of the tuned ports. For the front tuned port 310, in one example, lengthening the front port tube 360, decreasing its open area, and/or decreasing the resistance of the front acoustic resistor 367 correspondingly increases the magnitude of the front tuned port impedance 310i. Such a change also increases acoustic pressure in the front acoustic volume 278v and increases its resonance frequency, which minimizes the level of the intentional leak that the front tuned port 310 provides. Because the level of the intentional leak of the overall earbud is inversely proportional to the pressure in the ear canal acoustic volume 211v, minimizing the level of the intentional leak increases the maximum low frequency response of the audible signals 277 and maximizes amplitude of the biosignals 101 in the ear canal acoustic volume 211v.

For the rear tuned port 312, in another example, lengthening the rear tuned port tube 366, decreasing its open area, and/or decreasing the resistance of the rear acoustic resistor 369 correspondingly increases the magnitude of the rear tuned port impedance 312i. Such a change also increases acoustic pressure in the rear acoustic volume 279v and increases its resonance frequency, which minimizes the level of the intentional leak that the rear tuned port 312 provides. This can also increase the maximum low frequency response of the audible signals 277 and maximize amplitude of the biosignals 101 in the ear canal acoustic volume 211v.

In a similar vein, at the internal tuned port 311, lengthening the internal port tube 365, decreasing its open area, and/or decreasing the resistance of the internal acoustic resistor 368 correspondingly increases the magnitude of the internal tuned port impedance 311i. This minimizes the intentional leak that the internal tuned port 311 provides, thus increases the maximum low frequency response of the audible signals 277 and maximizes the amplitude of the biosignals 101 in the ear canal acoustic volume.

In yet another example, lengthening the nozzle 214, decreasing its open area, and/or decreasing the resistance of the nozzle resistor 370 correspondingly increases the magnitude of the nozzle impedance 214i. However, increasing the nozzle impedance 214i decreases the acoustic pressure in the ear canal acoustic volume 211v. This pressure decrease produces less amplification of the biosignals 101 in the ear canal 211 for detection by the infrasonic/vibration sensor 206, and causes roll off of the audible signals 277 and the biosignals 101 to begin at higher frequencies. As a result, the nozzle impedance 214i is preferably designed to be at least two orders of magnitude lower than the average impedance of the tuned ports 310-312.

A lower nozzle impedance 214i has additional benefits. It can dampen sharp peaks and dips in the audio response, does not significantly reduce the amplitude of the audible signals 277 presented to the ear canal 211, and does not significantly reduce the acoustic pressure in the ear canal acoustic volume 211v/reduce the amplitude of the biosignals 101 in the ear canal 211.

Designers must design the earbud 10 and its components so that the overall acoustic volume of the earbud 10 does not significantly increase the ear canal acoustic volume 211v, the result of which would decrease the acoustic pressure in the ear canal 211 and thus negatively impact biosignal 101 acquisition.

By way of example, a typical existing audio earbud is designed as follows. Its outermost cavity is on the order of 1/10 the size of the ear canal. The front cavity is similar though often slightly larger. Its speaker is more acoustically compliant than it is acoustically stiff. In more detail, the speaker typically has an effective acoustic volume that is more than twice that of the ear canal. Such a design is optimized for reproduction and enhancement of audible signals while reducing any occlusion effect upon the ear canal. Typical existing audio earbuds are also tuned/configured such that the transfer function of the earbuds 10 has a roll off of about 20 dB/decade below 20 Hz. Such a tuning significantly reduces the level of biosignals in the ear canal, the largest component of which is at around 1 Hz and has a very low signal to noise ratio (SNR) at that frequency.

In contrast, the proposed earbud 10 is tuned/designed to maximize its frequency response/transfer function below 20 Hz, which is the range of frequencies where the biosignals 101 dominate. At the same time, the earbud 10 is designed to maximize the low frequency response of the audible signals 277 that its speaker 208 presents. For this purpose, in one example, the speaker 208 of the earbud 10 is designed to be much more acoustically stiff/much less acoustically compliant than the speakers of typical existing audio earbuds. In another example, the tuned ports 310-312 are designed to have an overall effective impedance that is much greater than that of ports of typical existing audio earbuds.

The speaker 208 of the earbud 10 is designed to be much more acoustically stiff than the speakers of typical existing audio earbuds. A more acoustically stiff speaker 208 produces a smaller speaker effective acoustic volume 208v during operation. The speaker effective acoustic volume 208v is at least less than half of the ear canal acoustic volume 211v, in order to limit the effect on the level of the biosignals 101 in the ear canal acoustic volume 211v. As a result, in one example, the earbud 10 is tuned by selecting a speaker with a speaker effective acoustic volume 208v that is less than or equal to ½ that of the ear canal acoustic volume 211v.

In one example, experimentation has shown that maximizing the acoustical stiffness/minimizing the acoustic compliance of the speaker 208 provides the best biosignal performance while also increasing the effect of the intentional leaks provided by the internal tuned port 311. Such an acoustically stiff speaker can also minimize variance of the biosignals 101 detected over time.

In another example, tuning the earbud 10 to maximize the intentional leak provided by the internal tuned port 311 relative to the intentional leak provided by the nozzle 214, in a range of ratios between 1:1 and 4:1, has experimentally shown to provide the best audio reproduction with the lowest biosignal 101 loss. In this example, the sum of the intentional leaks provided by the nozzle 214, the front tuned port 310 and the rear tuned port 312 are maintained at a ratio of 1:2 compared to the unintentional leak 354'. Such a tuning provides consistent, maximal audio reproduction and biosignal performance.

In yet another example, minimizing the intentional leak provided by the front tuned port 310 maximizes biosignal performance, subject to constraints on insertion-caused overpressure on the diaphragm 356 of the speaker 208 and the infrasound/vibration sensor 206.

The levels of damping provided by the internal tuned port 311 and the front tuned port 310 are proportional to the audio response at low frequencies that the earbud 10 can provide. If the rear port tube 366 is small/the impedance of the rear tuned port 312 is large, the internal tuned port 311 provides minimal effect on the ability of the earbud 10 to sense biosignals 101. However, if the rear port tube 366 is large/the impedance of the rear tuned port 312 is small, the level of damping on the internal tuned port 311 becomes a critical component of preserving the detection of biosignals 101, as the internal tuned port 311 provides the primary leak path to the rear acoustic volume 279v and to the rear tuned port 312.

An example tuning that maximizes biosignal amplitude and thus acquisition while also maximizing response of the audio signals 277 at low frequencies is as follows. The front port tube 360 of the front tuning port 310 is closed/sealed. As a result, the front tuned port impedance 310i is infinite, and the front tuned port 360 thus introduces no intentional leak into the front acoustic volume 278v. At the same time, both the internal tuned port 311 and the rear tuned port 312 are tuned/configured to have impedances that provide intentional leaks into the front and rear acoustic volume 278v and 279v, respectively. In this example, the acoustic mass of the rear tuned port 312 is configured to be approximately three-fourths that of the acoustic mass of the front tuned port 310; the rear tuned port 312 has an acoustic resistance that is approximately twice that of the acoustic resistance of the front tuned port 310; and an open area of the acoustic resistors 367-369 of the tuned ports 310-312 is the same as the open area of each respective port tube 360, 365, and 366.

The open area of the resistors/port tube is defined as follows. It is an area of the interface between the opening of each port tube, and the adhesive that holds its respective acoustical resistor in place and disposed against the port tube. The acoustic resistors are formed of a resistive material with a calibrated resistance. The open area of each acoustic resistor can be changed during design of the earbud, thereby affecting the added acoustic resistance, as the specific acoustic resistance is defined as resistance per unit area.

In other embodiments, the earbud 10 can include less than the three tuned ports 310, 311, and 312. In some implementations, only one of the tuned ports 310, 311, 312 are included. In other implementations, two of any of the tuning ports are included.

In this way, the earbud also forms a vibroacoustic apparatus. The vibroacoustic apparatus includes a housing 204 having an interior and a nozzle 214 configured to be positioned within the ear canal 211 of the individual 99 during use, where the nozzle 214 forms a nozzle opening 201 configured to receive infrasonic and non-infrasonic signals, and the housing 204 defines a front acoustic volume 278v and a rear acoustic volume 279v. The vibroacoustic apparatus also includes an infrasonic/vibration sensor 206 within the nozzle 214 that is configured to detect biosignals 101 including infrasonic biosignals from the body of the individual 99, and includes a plurality of additional openings through the housing 204 that together provide a fluid pathway from the rear acoustic volume 279v to the front acoustic volume 278v and into the ear canal 277 via the nozzle opening 201.

In more detail, the nozzle 214 is also configured to form a seal 354 around the nozzle 214 with the ear canal 211 during use that allows acoustic pressure to increase in the ear canal. The fluid pathway is configured to form an acoustic leak that contributes to the acoustic pressure within the ear canal during use, and the fluid pathway is configured to control the ear canal acoustic pressure to at least in part offset a leak in the seal 354 to enhance a fidelity of the infrasonic biosignals.

Figure 4:
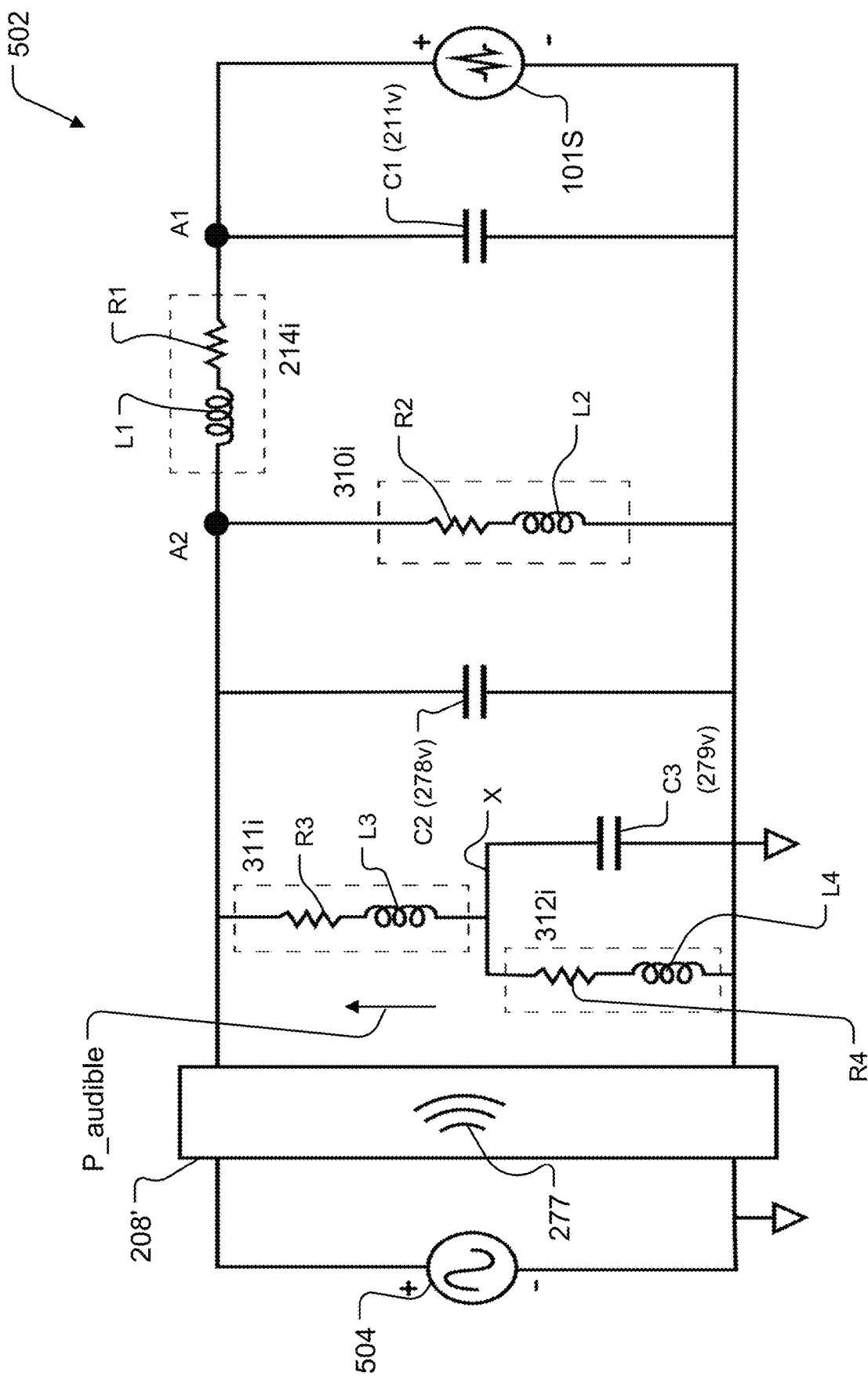
FIG. 4 is an equivalent electrical circuit for the mechano-acoustical system of the earbud in FIG. 3, where the electrical circuit models the behavior of the mechano-acoustical system and its components using principles of duality.

FIG. 4 is an equivalent electrical circuit 502 for the mechano-acoustical system 300 of the earbud 10 described in FIG. 3. The electrical circuit 502 models the behavior of the components within the mechano-acoustical system 300 using principles of duality.

The circuit 502 includes various circuit components that "map" to corresponding physical components and acoustic volumes in the earbud 10 of FIG. 3. These circuit components include an alternating voltage source 504, a speaker model 208', capacitors C, inductors L, resistors R, and a biosignal voltage source 101S. Each component contributing acoustical mass and resistance can be represented as associated electrical components in series in the electrical circuit 502. Specifically, the effective acoustical resistance of a component is represented as a resistor R, and its effective acoustical mass is represented as an inductor L. The speaker effective acoustic volume 208$v$ is represented as the speaker model 208'. The other acoustic volumes 278$v$, 279$v$, and 211$v$ are modeled as capacitors C.

The circuit 502 also includes circuit nodes A1 and A2. The acoustic pressure in the ear canal acoustic volume 211$v$ is represented by node A1, while the acoustic pressure observed by the infrasonic/vibration sensor 206 is represented by node A2. The alternating voltage source 504 powers the speaker model 208' and the biosignal voltage source 101S supplies an assumed biosignal acoustic pressure. Both sources may be driven simultaneously or alone.

The alternating voltage source 504 represents the input electrical signals provided to the speaker 208 by the audio source. The direction of the voltage is from negative (−) to positive (+). The pressure created by the speaker 208 when presenting its audible signals 277, and its direction, is indicated by reference P_audible. The effective acoustic volume 208$v$ of the speaker 208 is incorporated within the speaker model 208' shown in the figure. The pressure that the biosignals 101 add to the ear canal acoustic volume 211$v$ is represented by the biosignal voltage source 101S.

From an impedance point of view, the circuit components that represent the acoustic volumes 208$v$, 211$v$, 278$v$, 279$v$, and 211$v$ are in parallel with one another. This results in an equivalent acoustic volume of the electrical circuit 502 that is proportional to the sum of: the ear canal acoustic volume 211$v$, the speaker effective acoustic volume 208$v$, the front acoustic volume 278$v$ and the rear acoustic volume 279$v$.

Circuit node A1 connects the biosignal voltage source 101S, resistor R1, inductor L1 and capacitor C1. R1 and L1 are in series and respectively represent the effective acoustical resistance and mass of the nozzle impedance 214$i$. Capacitor C1 represents the ear canal acoustic volume 211$v$ and is in parallel with the L1/R1 series combination.

Circuit node A2 connects the alternating voltage source 504, the speaker model 208', resistors R2-R4, inductors L2-L4 and capacitors C2, C3. In more detail, R2 and L2 are in series and respectively represent the effective acoustical resistance and mass of the front tuned port impedance 310$i$; R3 and L3 are in series and respectively represent the effective acoustical resistance and mass of the internal tuned port impedance 311$i$; and R4 and L4 are in series and respectively represent the effective acoustical resistance and mass of the rear tuned port impedance 312$i$. C2 and C3 respectively represent the front and rear acoustic volumes 278$v$, 279$v$.

The circuit elements in node A2 are arranged as follows. C3 is in parallel with the R4/L4 series combination that represents the rear tuned port impedance 312$i$. This parallel combination is indicated by reference X. The parallel combination X, in turn, is in series with the R3/L3 series combination. Finally, the circuit segment that includes the series combination of R3/L3 and X is in parallel with C2 and R2/L2.

Figure 5:
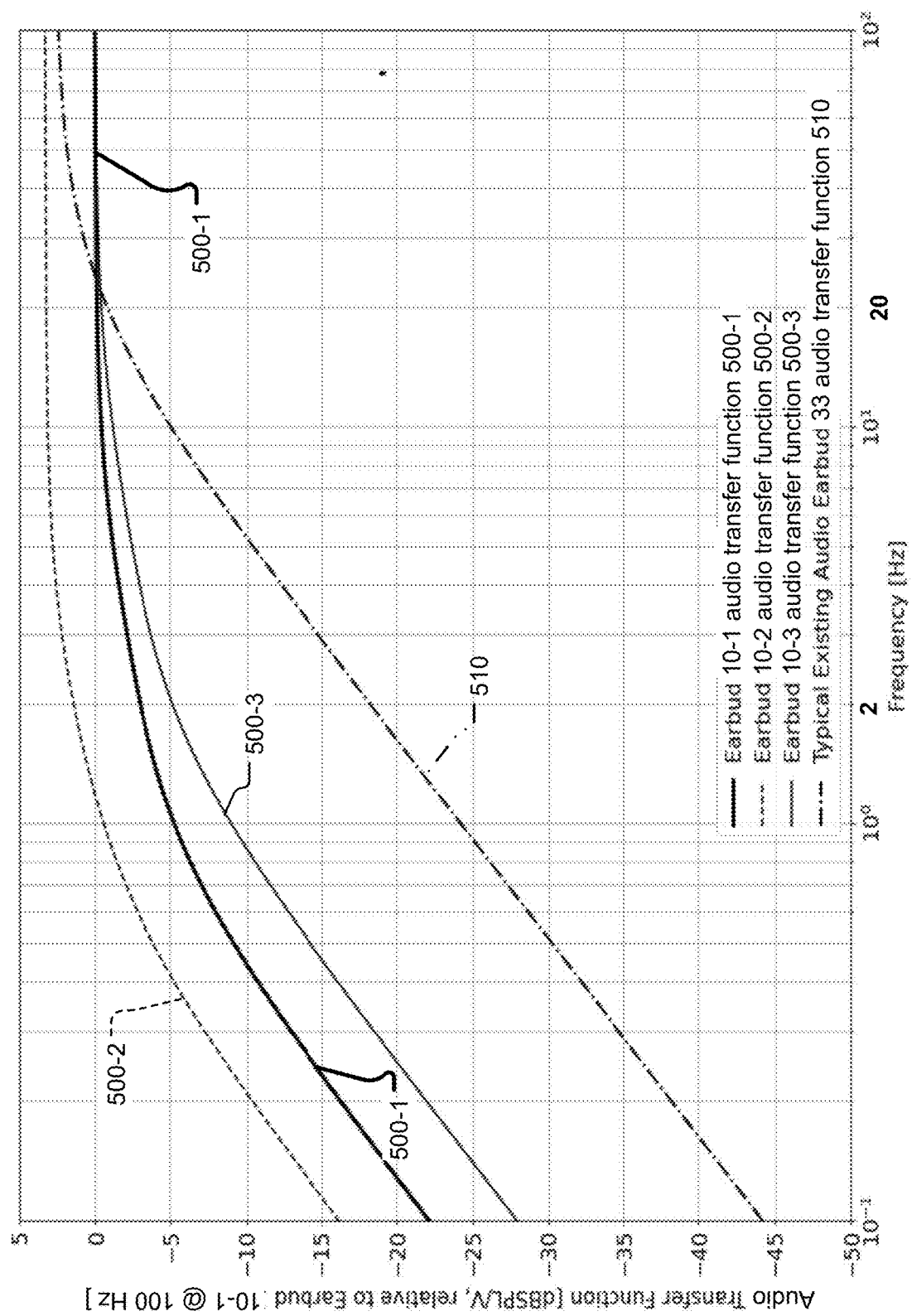
FIG. 5 shows plots of predicted audio transfer functions for different implementations of the proposed earbud and for a typical existing audio earbud, over a frequency range of 0 to 100 Hz, where each of the audio transfer functions plot an audio frequency response that relates voltage applied at the speaker to an acoustic pressure in the ear canal detected by the sensor, and where the acoustic pressure in the ear canal is produced by the audible signals presented by the speaker.

FIG. 5 shows different predicted audio transfer functions (acoustic pressure in the occluded ear canal per volt of excitation at the speaker) for three different embodiments of the proposed earbud 10 and for a typical existing audio earbud 33. These embodiments of the earbud 10 are indicated by references 10-1, 10-2, and 10-3 and their respective audio transfer functions are indicated by references 500-1, 500-2 and 500-3. The audio transfer function of the typical existing audio earbud 33 is indicated by reference 510. Each of the embodiments of the earbud 10 include the same components and operate in substantially the same way but are tuned differently for comparison.

The typical existing audio earbud 33 is assumed to have approximately the same size housing and the same number and location of tuned ports as the earbuds 10-1 through 10-3. However, because the typical existing audio earbud 33 is designed solely for audio performance, its speaker is much more acoustically compliant and thus has a much larger speaker effective acoustic volume than the earbuds 10-1 through 10-3, and its tuned ports have a much smaller overall impedance than the tuned ports of the earbuds 10-1 through 10-3.

The audio transfer functions 500-1 through 500-3 for earbuds 10-1 through 10-3 and the audio transfer function 510 for the typical existing audio earbud 33 were calculated based on equivalent circuits 502 created for each. The equivalent circuits were created in accordance with the duality principles provided in the description that accompanies FIG. 4, included herein above.

The predicted audio transfer functions 500-1 through 500-3 plot a predicted audio frequency response of the infrasonic vibration sensor 206 to the input voltage 504 applied to the speaker 206. The units of the audio transfer function are expressed in decibels of sound pressure level per volt (dBSPL/V). The audio transfer function 510 for the typical existing audio earbud is plotted in a similar fashion using its audio microphone. For purposes of illustration, each audio transfer function was computed, and then normalized by the value of the audio transfer function 500-1 of earbud 10-1 at 100 Hz; only a portion of each audio transfer function between 0.1 Hz and 100 Hz is shown.

More detail for the tuning of each of the earbuds 10-1 through 10-3 is as follows. Earbud 10-1 is tuned/constructed such that the front port tube 367 of its front tuned port 310 is sealed. The internal port tube 365 of the internal tuned port 311 remains open, which mitigates buckling of the suspension system of the speaker 206 during operation. An arbitrary value is selected for the front tuned port impedance 310$i$, and the rear tuned port impedance 312$i$ is selected to be twice that of the front tuned port impedance 310$i$. It was also assumed that the level of the earbud seal 354 was very high (i.e., a negligible amount of unintentional leak 354' was present).

Earbud 10-2 is tuned to have an overall acoustic volume that is twice that of earbud 10-1. Earbud 10-3 is tuned to have an overall tuned port impedance that is half that of earbud 10-1.

The overall acoustic volume of each earbud 10 is a weighted sum of its front acoustic volume 278$v$, rear acoustic volume 279$v$, and speaker effective acoustic volume 208$v$. The overall tuned port impedance of each earbud 10 is the sum of its front, internal, and rear tuned port impedances 310$i$, 311$i$, 312$i$ and its nozzle impedance 214$i$. Here, the overall tuned port impedance for earbud 10-3 was selected by reducing each of the tuned port impedances of earbud 10-1 by half.

The typical existing audio earbud 33 is modeled as follows. Compared to the earbud 10-1, the speaker effective acoustic volume of the typical existing audio earbud 33 was selected to be much higher (specifically, an order of magnitude higher) and the overall tuned port impedance of the earbud 510 was selected to be much lower (specifically, an order of magnitude lower). As with earbuds 10-1 through 10-3, it was also assumed that the level of the earbud seal was high (i.e., a negligible amount of unintentional leak was present).

In the illustrated example, the audio transfer function 500-1 for earbud 10-1 has the following characteristics. It has a roll off that begins at approximately 10 Hz. However, between 10 Hz and 1 Hz, the roll off has a shallow negative slope and drops no more than 5 dB over that range. It has a normalized response between −2 dB and −22 dB over a frequency range between 2 Hz and 20 Hz, respectively. Between 3 Hz and 1 Hz, in particular, the roll off drops no more than 3 dB over that range. This provides an exceptional balance between preserving audio performance magnitude and minimizing its variation among manufactured earbuds while also maximizing infrasound reproduction.

The audio transfer function 500-2 for earbud 10-2 shows the effect of increasing the overall acoustic volume of the earbud by a factor of 2, as compared to earbud 10-1. In more detail, the shape of audio transfer function 500-2 is substantially similar to that of the audio transfer function 500-1 of earbud 10-1, with a substantially similar shaped roll off. However, its roll off starts at a lower frequency, at around 4 Hz. Moreover, it has an improved frequency response of at least 3 dB across the entire 0 to 100 Hz selected frequency portion. In particular, the transfer function 500-2 of earbud 10-2 has a normalized response between 2 dB and −16 dB, over a frequency range between 2 Hz and 0 Hz, respectively.

The audio transfer function 500-3 for earbud 10-3 shows the effect of decreasing the overall impedance of the tuned ports by half, as compared to earbud 10-1. In more detail, the shape of audio transfer function 500-3 is substantially similar to the audio transfer function 500-1 of earbud 10-1. Its roll off starts at a higher frequency, at about 20 Hz, but its roll off has a substantially similar shape. Compared to the audio transfer function 500-1 of earbud 10-1, the audio transfer function 500-3 of earbud 10-3 has a frequency response that is decreased by about 3 dB between 0 and 2 Hz, and then is substantially the same between 2 Hz and 100 Hz. In particular, the audio transfer function 500-3 of earbud 10-3 has a normalized response between −5 dB and −27 dB, over a frequency range between 2 Hz and 0 Hz, respectively.

The audio transfer function 510 for the typical existing audio earbud 33 has the following characteristics. It illustrates the effect that a significant increase in the acoustic volume of the earbud and a significant decrease in its overall tuned port impedance has, as compared to earbud 10-1. While the frequency response at audible frequencies (above 20 Hz) is slightly increased, the audio performance below 20 Hz is significantly decreased. The roll off starts at a much higher frequency (here, around 75 Hz). The slope of its roll off is more negatively steeper and is nearly linear over the frequency range 0 Hz to 20 Hz. The audio transfer function has a normalized response between 0 dB and −45 dB, over a frequency range between 20 Hz and 0 Hz, respectively.

In particular, the audio transfer function 510 of the typical existing audio earbud 33 has a normalized response between −18 dB and −45 dB, over a frequency range between 2 Hz and 0 Hz, respectively. At 1 Hz, for example, the frequency response is approximately −25 dB. In contrast, the audio frequency response of earbud 10-1 at 1 Hz is −5 dB, which is at least two orders of magnitude greater. This significantly lower frequency response 510 for the typical existing audio earbud 33 is expected, as it is not designed to reproduce infrasounds/sounds below the range of human hearing.

In general, the audio frequency response 500 of the earbud 10 at 1 Hz has been experimentally shown to be in a range between −15 dB and 0 db.

Figure 6:
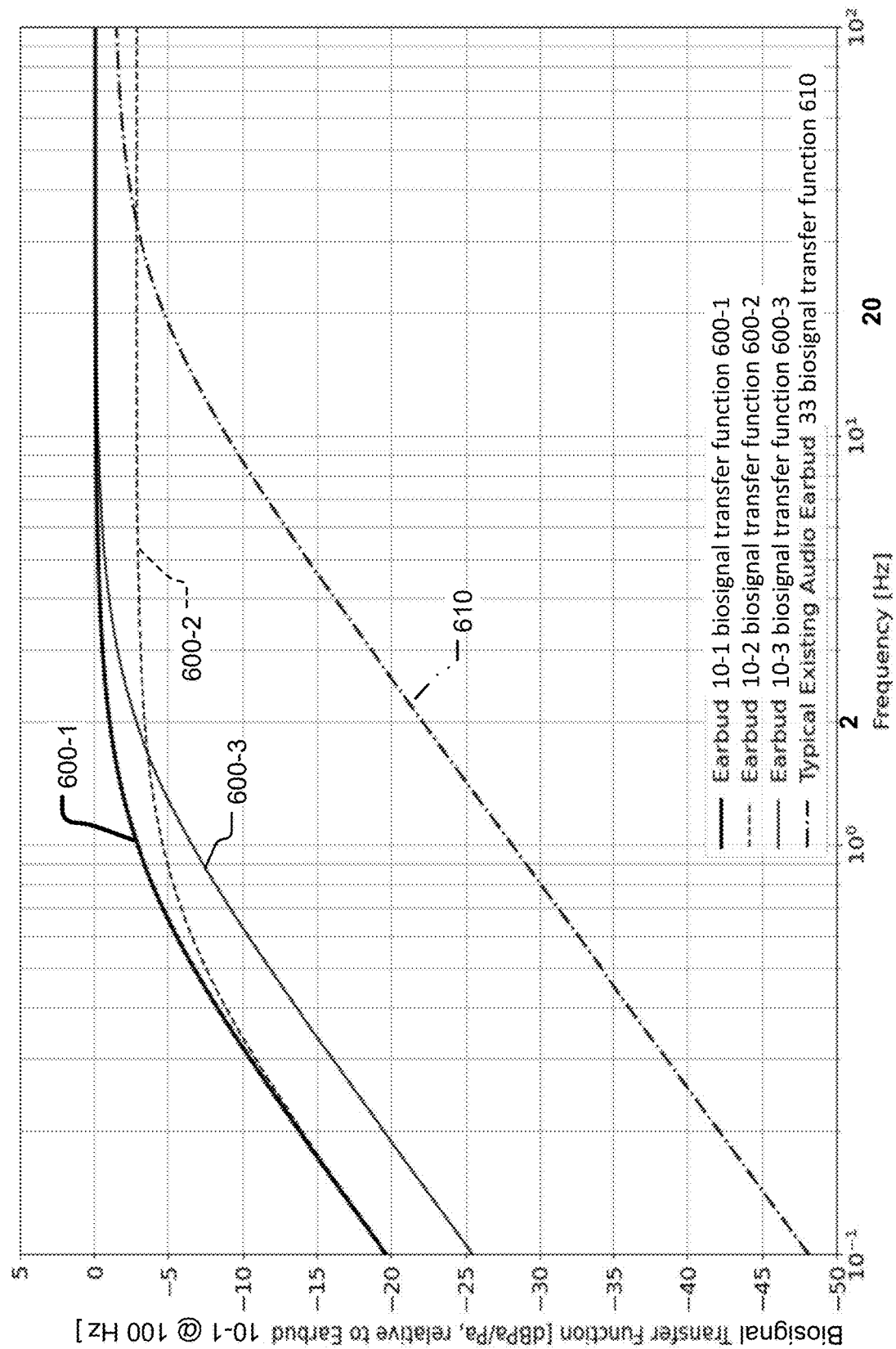
FIG. 6 shows plots of predicted biosignal transfer functions for the same earbuds in FIG. 5 over the same frequency range, where each of the biosignal transfer functions plot a biosignal frequency response that relates an acoustic pressure detected by the sensor to the acoustic pressure in the ear canal.

FIG. 6 shows different biosignal transfer functions (acoustic pressure at the sensor per unit of biosignal acoustic pressure). Three biosignal transfer functions 600-1, 600-2, and 600-3 are respectively calculated for the same earbuds 10-1, 10-2 and 10-3 and a biosignal transfer function 610 is calculated for the typical existing audio earbud 33. Each of the earbuds 10-1, 10-2 and 10-3 are respectively tuned in the same way as previously disclosed in the description associated with FIG. 5.

Here, each of the biosignal transfer functions 600-1 through 600-3 for the earbuds 10-1 through 10-3 plot the predicted magnitude of the low frequency response of the infrasonic/vibration sensor 206, versus the acoustic pressure exerted by the biosignals 101 observed in the ear canal acoustic volume, and are normalized by the magnitude of the biosignal transfer function 600-1 of earbud 10-1 at 100 Hz. For the typical existing audio earbud 33, the biosignal transfer function 610 plots the predicted magnitude of the low frequency response of its audio sensor/microphone to the acoustic pressure exerted by the biosignals 101, the result of which is also normalized by the magnitude of the biosignal transfer function 600-1 of earbud 10-1 at 100 Hz. Each biosignal transfer function 600, 610 was calculated when its associated earbud was sealed to a 2 cc coupler.

The biosignal transfer functions 600-1 through 600-3 for earbuds 10-1 through 10-3 and the biosignal transfer function 610 for the typical existing audio earbud 33 are calculated based on an equivalent circuit model 502 created for each earbud. As in FIG. 5, only the portion of the transfer functions between 0.1 and 100 Hz are displayed. It was also assumed that the level of the earbud seal was high (i.e., a negligible amount of unintentional leak was present).

The biosignal transfer function 600-1 for earbud 10-1 has the following characteristics. While it has a low-frequency roll off that starts above 1 Hz (specifically, at about 3 Hz), its frequency response drops only 3 dB between 3 Hz and 1 Hz. This is important, as the normal fundamental frequency of an individual's average heart rate, (an example of a desired biosignal 101) is typically between 1 Hz and 2 Hz. Thus, the biosignal transfer function 600-1 shows that the earbud 10-1 has minimal fundamental signal loss of biosignals 101 and near-complete preservation of the harmonics of the biosignals 101.

The biosignal transfer function 600-2 for earbud 10-2 has the following characteristics as compared to the biosignal transfer function 600-1 for earbud 10-1. The shape of the biosignal transfer function 600-2 is substantially similar to that of the biosignal transfer function 600-1 of earbud 10-1. Its response is about 3 dB lower in a frequency range between about 0.8 Hz and 100 Hz, and is nearly identical below 0.8 Hz. Its roll off starts at a lower frequency, at around 1 Hz. Its response drops 3 dB between the start of its roll off and 0.8 Hz.

The biosignal transfer function 600-3 for earbud 10-3 has the following characteristics as compared to the biosignal transfer function 600-1 for earbud 10-1. Its shape is substantially similar. Its response is about 3 dB lower in a frequency range between about 3 Hz and 0 Hz, and is nearly identical above 3 Hz. Its roll off starts at a higher frequency, at around 8 Hz, and its response drops 3 dB between the start of its roll off and approximately 1.7 Hz.

In contrast, the biosignal transfer function 610 for the typical existing audio earbud 33 has a roll off that starts at about 75 Hz. Between 75 Hz and 20 Hz, the slope of the roll off is shallow with a drop of only 3 dB. Between 20 Hz and 0 Hz, however, the slope of the roll off is steeper than the earbuds 10 and is nearly linear. At 2 Hz, for example, the frequency response is about -22 dB. The biosignal transfer function 610 for the typical existing audio earbud 33 illustrates that the earbud 33 is not designed for acquisition of biosignals 101.

In general, the biosignal frequency response 600 of the earbud 10 at 1 Hz has been experimentally shown to be in a range between −15 dB and 0 db.

FIG. 7A shows amplitude plots of biosignals 101 of an individual 99, obtained by both the earbud 10-1 and an electrocardiogram (ECG) 702 over the same time frame.

The ECG 702 is generally considered to be the standard for measuring heart rate and function. The heartbeat is the time between successive peaks 702p in the ECG. Periodic QRS complexes that electrically detect ventricular depolarization are also shown.

Peaks 10-1p in the plot of the earbud 10-1 track that of the peaks 702p of the ECG 702, and can also very accurately determine the heartbeat of the individual 99. With the exception of the QRS complex in the ECG plot, the waveform of the earbud 10-1 plot has substantially the same shape as the plot of the ECG, indicating that there is negligible signal variation in the plot of the earbud 10-1 over time. Moreover, aside from the QRS complex, the information of which the earbud 10-1 does not detect directly, the plot of the earbud 10-1 includes significantly more signal information between heartbeats than the ECG 702. This enhanced signal information is indicated by reference 704.

FIG. 7B shows amplitude plots of biosignals 101 of an individual 99, obtained by both the typical existing audio earbud 33 and an ECG 702 over the same time frame. The plot of the typical existing audio earbud 33 is effectively flat and carries very little signal information. Periodic peaks 33p in the plot of the typical existing audio earbud 33 are barely discernible, if at all, from the rest of the signal.

Figure 8:
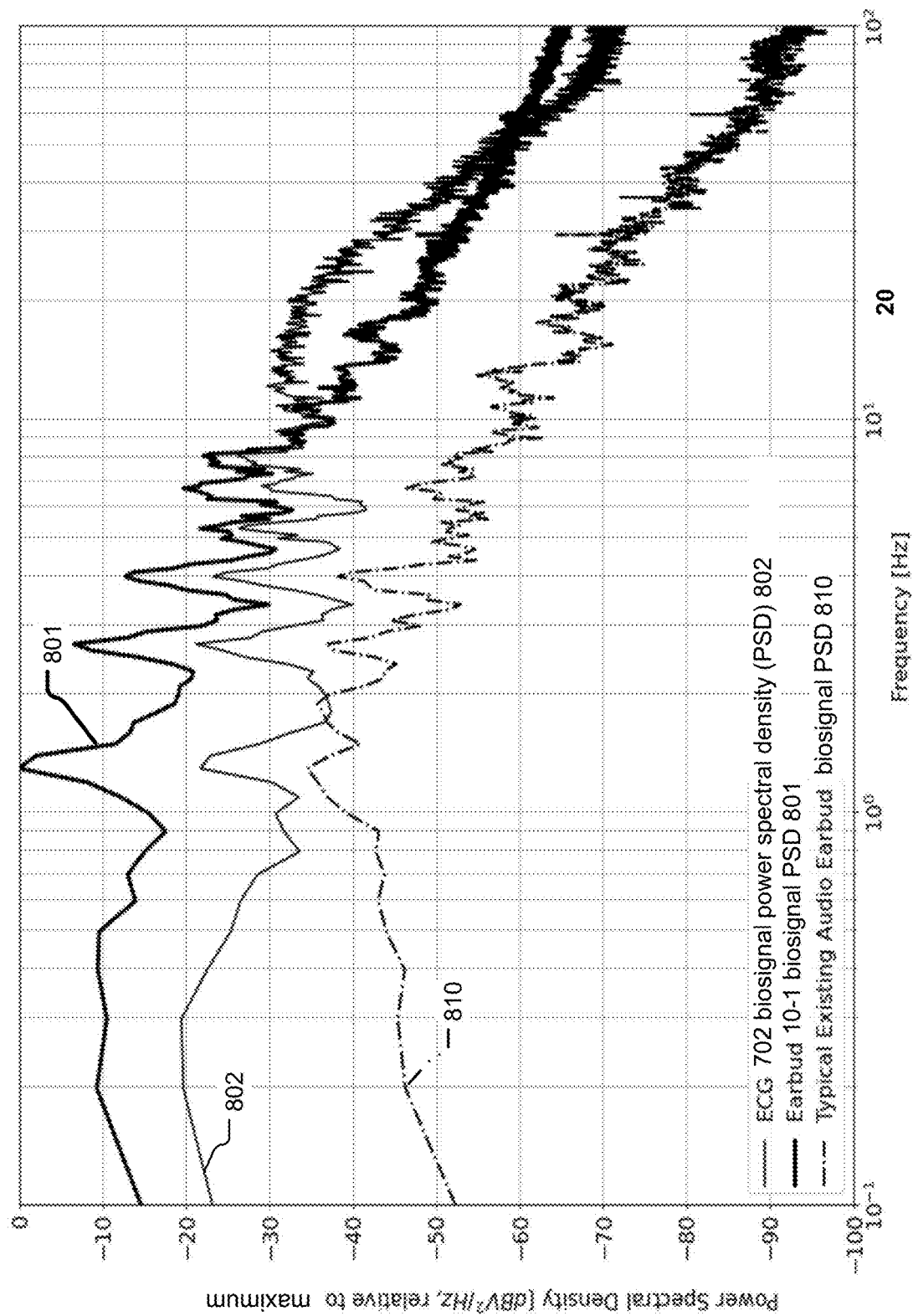
FIG. 8 shows long-term-averaged power spectral density (PSD) plots of biosignals obtained from an exemplary proposed earbud, from a typical existing audio earbud, and from an ECG for the same individual, over the same time frame.

FIG. 8 shows averaged power spectral density (PSD) plots of biosignals 101 for the same individual 99, obtained by an ECG 702, the earbud 10-1 and a typical existing audio earbud 510, over the same time period. The biosignal PSD for the earbud 10-1, the ECG 702, and the typical existing audio earbud 510 are indicated by references 801, 802, and 810, respectfully. The biosignals were obtained over a two-minute period, and a frequency portion of the plots between 0.1 Hz and 100 Hz is shown, relative to the maximum PSD value observed.

With reference to the plots in FIG. 8, the biosignal PSD 801 of earbud 10-1 has a higher value/frequency response for frequencies between 1 Hz and 10 Hz than the biosignal PSD 802 of the ECG 702 and the biosignal PSD 810 of the typical existing audio earbud 33. The biosignal PSD 801 of earbud 10-1 also includes more signal information, at the very least within the infrasonic frequency range.

In one example, details found in the biosignals 101 obtained from earbud 10-1 plotted in FIG. 7A, the biosignal PSD 801 of earbud 10-1 in FIG. 8, and the transfer functions 500-1, 600-1 of earbud 10-1 in FIGS. 5 and 6 can assist in the diagnosis of multiple heart conditions. Because the plots of the biosignals 101 obtained from the earbud 10-1 and its biosignal PSD 801 can include information that meets or exceeds that of the ECG 702 and its biosignal PSD 802, it is suggested that the earbud 10 is a viable candidate to possibly replace the ECG as the standard for heart monitoring.

While this invention has been particularly shown and described with references to preferred embodiments thereof, it will be understood by those skilled in the art that various changes in form and details may be made therein without departing from the scope of the invention encompassed by the appended claims.

What is claimed is:

1. A vibroacoustic apparatus, comprising:
    a housing having an interior and a nozzle configured to be positioned within an ear canal of an individual during use, the nozzle forming a nozzle opening configured to receive infrasonic and non-infrasonic signals, the nozzle configured to form a seal around the nozzle with the ear canal during use that allows acoustic pressure to increase in the ear canal, the housing defining a front acoustic volume and a rear acoustic volume;
    an infrasonic/vibration sensor within the nozzle configured to detect biosignals including infrasonic biosignals from the body of the individual in the ear canal; and
    a plurality of additional openings through the housing that together provide a fluid pathway from the rear acoustic volume to the front acoustic volume and into the ear canal via the nozzle opening, the fluid pathway being configured to form an acoustic leak that contributes to the acoustic pressure within the ear canal during use, the fluid pathway configured to control the ear canal acoustic pressure to at least in part offset a leak in the seal to enhance a fidelity of the infrasonic biosignals.

2. The vibroacoustic apparatus of claim 1, further comprising an acoustic resistor coupled with at least one of the additional openings.

3. The vibroacoustic apparatus of claim 1, wherein the plurality of additional openings includes a front opening fluidly connecting the front acoustic volume with the interior, and a back opening fluidly connecting the rear acoustic volume with the interior.

4. The vibroacoustic apparatus of claim 1, wherein the plurality of additional openings includes an internal opening fluidly connecting the front acoustic volume with the rear acoustic volume, wherein an acoustic leak provided by the internal opening relative to an acoustic leak provided by the nozzle is in a range of ratios between 1:1 and 4:1.

5. The vibroacoustic apparatus of claim 1 having an associated audio transfer function with a roll off between -15 dB and 0 dB at 1 Hz.

6. The vibroacoustic apparatus of claim 5, wherein the roll off between 10 Hz and 1 Hz has a negative slope of no greater than 5 dB.

7. The vibroacoustic apparatus of claim 1 having an associated biosignal transfer function with a roll off between -15 dB and 0 dB at 1 Hz.

8. The vibroacoustic apparatus of claim 7, wherein a -3 dB frequency of the roll off is approximately 3 Hz.

9. The vibroacoustic apparatus of claim 7, wherein the roll off between 3 Hz and 1 Hz has a negative slope of no greater than 3 dB.

10. The vibroacoustic apparatus of claim 1, wherein the acoustic pressure in the ear canal is at least partially produced by the biosignals in the ear canal.

11. A method for a vibroacoustic apparatus including a housing, the housing having an interior, the method comprising:

positioning a nozzle of the apparatus within an ear canal of an individual during use, the nozzle forming a nozzle opening configured to receive infrasonic and non-infrasonic signals, the nozzle configured to form a seal around the nozzle with the ear canal during use that allows acoustic pressure to increase in the ear canal, the housing defining a front acoustic volume and a rear acoustic volume;

detecting biosignals including infrasonic biosignals from the body of the individual in the ear canal via an infrasonic/vibration sensor within the nozzle; and a plurality of additional openings through the housing, together providing a fluid pathway from the rear acoustic volume to the front acoustic volume and into the ear canal via the nozzle opening, the fluid pathway being configured to form an acoustic leak that contributes to the acoustic pressure within the ear canal during use, the fluid pathway controlling the ear canal acoustic pressure to at least in part offset a leak in the seal to enhance a fidelity of the infrasonic biosignals.

12. The method of claim 11, further comprising coupling an acoustic resistor with at least one of the additional openings.

13. The method of claim 11, further comprising the plurality of additional openings including a front opening fluidly connecting the front acoustic volume with the interior, and a back opening fluidly connecting the rear acoustic volume with the interior.

14. The method of claim 11, wherein the plurality of additional openings includes an internal opening fluidly connecting the front acoustic volume with the rear acoustic volume, wherein an acoustic leak provided by the internal opening relative to an acoustic leak provided by the nozzle is in a range of ratios between 1:1 and 4:1.

15. The method of claim 11 having an associated audio transfer function with a roll off between -15 dB and 0 dB at 1 Hz.

16. The method of claim 15, wherein the roll off between 10 Hz and 1 Hz has a negative slope of no greater than 5 dB.

17. The method of claim 11 having an associated biosignal transfer function with a roll off between -15 dB and 0 dB at 1 Hz.

18. The method of claim 17, wherein a -3 dB frequency of the roll off is approximately 3 Hz.

19. The method of claim 17, wherein the roll off between 3 Hz and 1 Hz has a negative slope of no greater than 3 dB.

20. The method of claim 11, the acoustic pressure in the ear canal being at least partially produced by the biosignals in the ear canal.

* * * * *